United States Patent [19]

Kempe et al.

[11] Patent Number: 5,117,004
[45] Date of Patent: May 26, 1992

[54] PREPARATION OF IMIDAZOLE-2-CARBOXYLIC ACIDS

[75] Inventors: Uwe Kempe, Dannstadt-Schauernheim; Toni Dockner, Meckenheim; Hermann Koehler, Beindersheim, all of Fed. Rep. of Germany

[73] Assignee: BASF Aktiengesellschaft, Ludwigshafen, Fed. Rep. of Germany

[21] Appl. No.: 309,089

[22] Filed: Feb. 10, 1989

[30] Foreign Application Priority Data

Feb. 13, 1988 [DE] Fed. Rep. of Germany ....... 3804545

[51] Int. Cl.$^5$ .................. C07D 235/30; C07D 435/30
[52] U.S. Cl. ..................... 548/323; 548/331; 548/337; 548/343
[58] Field of Search ................ 548/343, 337, 323, 331

[56] References Cited

U.S. PATENT DOCUMENTS 4,179,277 12/1979 Beck et al. .................. 71/92
4,369,186 1/1983 Beck et al. .................. 424/273
4,672,128 6/1987 Kemp et al. .................. 548/343

FOREIGN PATENT DOCUMENTS 0172407 2/1986 European Pat. Off. .
1033667 7/1958 Fed. Rep. of Germany .
2634053 2/1978 Fed. Rep. of Germany .

OTHER PUBLICATIONS

Journal of the Chemical Society, vol. CXV., pp. 217-260 (1919).
A. Bistrzycki, et al., *Chem. Ber.* 45 (1912), 3483.
J. Dirlam et al., *J. Heterocycl. Chem.* 17 (1980), 409-411.
B. Iddon, et al., *Tetrahedron Letters* 27 (1986), 1635-1638.
S. Roseman, *J. Amer. Chem. Soc.* 75 (1953) 3854.

*Primary Examiner*—Johann Richter
*Attorney, Agent, or Firm*—Keil & Weinkauf

[57] ABSTRACT

4,5-Disubstituted imidazole-2-carboxylic acids are prepared by reacting 4,5-disubstituted imidazoles with carbon dioxide under superatmospheric pressure at from 150° to 300° C. in the presence of a base.

7 Claims, No Drawings

PREPARATION OF IMIDAZOLE-2-CARBOXYLIC ACIDS

The present invention relates to a novel process for preparing 4,5-disubstituted imidazole-2-carboxylic acids by reacting 4,5-disubstituted imidazoles with carbon dioxide under superatmospheric pressure at from 150° to 300° C. in the presence of a base.

The present invention further relates to novel 4,5-disubstituted imidazole-2-carboxylic acids.

The literature discloses the following ways of preparing benzimidazole-2-carboxylic acids:

condensation of o-phenylenediamine with glycolic acid to give 2-hydroxymethylbenzimidazole and subsequent oxidation with $KMnO_4$ (A. Bistrzycki, G. Przeworski, Chem. Ber. 45 (1912), 3483) and condensation of 2-methylbenzimidazole with benzaldehyde to the styryl compound and subsequent oxidation with $KMnO_4$ (S. Roseman, J. Amer. Chem. Soc. 75 (1953), 3854).

DE-A-1,033,667 discloses the reaction of imidazole with $CO_2$ under superatmospheric pressure, which gives imidazole-4(5)-carboxylic acid or imidazole-4,5-di-carboxylic acid. EP-A-172,407 discloses the analogous reaction with imidazole compounds which are unsubstituted in the 4- and 5-positions and various imidazole compounds which are monosubstituted in the 4(5)-position. Here the carboxyl group enters the imidazole ring in all cases only in position 4 (or 5).

Besides the imidazoles known from the aforementioned documents, 4,5-dichloro- and 4,5-dibromo-imidazole-2-carboxylic acid are known from DE-A-2,610,527, DE-A-2,634,053, Tetrahedron Letters 27 (1986), 1635-1638, and J. Heterocycl. Chem. 17 (1980), 409-411.

It is an object of the present invention to find a new and better way of obtaining 4,5-disubstituted imidazole-2-carboxylic acids.

We have found that this object is achieved with a novel process for preparing a 4,5-disubstituted imidazole-2-carboxylic acid, which comprises reacting a 4,5-disubstituted imidazole with carbon dioxide under superatmospheric pressure at from 150° to 300° C. in the presence of a base.

4,5-Disubstituted imidazole-2-carboxylic acids are obtainable by the following method:

The reaction takes place between a 4,5-disubstituted imidazole and carbon dioxide under superatmospheric pressure at from 150° to 300° C. in the presence of a base in accordance with the following reaction equation:

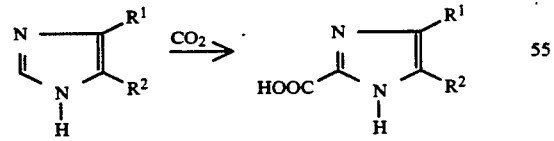

The reactions are preferably carried out at from 150° to 300° C., particularly preferably at from 180° to 280° C., and under pressures of from 10 to 300 bar, preferably of from 10 to 180 bar, particularly preferably at from 40 to 180 bar.

The process may be carried out continuously or batchwise.

In general, the reaction is carried out under superatmospheric pressure and in the absence of a solvent.

4,5-Disubstituted imidazoles are mostly known and may be prepared by the methods described in K. Hofmann, Imidazole and its Derivatives, Interscience, New York 1953, p. 33 ff.

The molar ratio of carbon dioxide : 4,5-disubstituted imidazole is from 1:1 to 100:1, preferably from 1:1 to 10:1.

The carbon dioxide may be used for example in gaseous, liquid or solid form. Liquid carbon dioxide is preferred.

However, the reaction may also be carried out in the presence of a solvent or diluent.

Suitable solvents or diluents are for example aliphatic hydrocarbons such as n-pentane, n-hexane, mixed hexane isomers and petroleum ether, halogenated hydrocarbons such as chlorobenzene, methylene chloride, ethylene chloride, chloroform and tetrachloroethylene, aromatic hydrocarbons such as benzene, toluene, the xylenes and mixed isomers thereof, and naphtha, ethers such as diethyl ether, di-n-butyl ether, methyl tert.-butyl ether, tetrahydrofuran and dioxane, and aprotic dipolar solvents such as dimethylformamide, N-methylpyrrolidone or tetramethylurea. It is also possible to use mixtures of these substances as solvents/diluents.

The reaction time is normally from 1 to 20 hours, usually from 2 to 12 hours.

The product can be isolated in a conventional manner. To this end, the crude product is added to water, the solution is brought to pH 2-6 with inorganic acids at from 10° to 60° C. The precipitated product can subsequently be isolated by filtration. The inorganic acids used are preferably hydrochloric acid, sulfuric acid or phosphoric acid.

The substituents $R^1$ and $R^2$ and the indices n and m in the formula I independently of one another preferably have the following meanings for the process:

$R^1$ and $R^2$
unbranched or branched $C_1$–$C_{20}$-alkyl, preferably unbranched or branched $C_1$–$C_{12}$-alkyl, such as methyl, ethyl, n-propyl, iso-propyl, n-butyl, iso-butyl, sec.-butyl, tert.-butyl, n-pentyl, iso-pentyl, sec.-pentyl, tert.-pentyl, neo-pentyl, 1,2-dimethylpropyl, n-hexyl, iso-hexyl, sec.-hexyl, n-heptyl, iso-heptyl, n-octyl, iso-octyl, n-nonyl, iso-nonyl, n-decyl, iso-decyl, n-undecyl, iso-undecyl, n-dodecyl and iso-dodecyl, unbranched or branched $C_2$–$C_{20}$-alkoxyalkyl, preferably unbranched or branched $C_2$–$C_8$-alkoxyalkyl, such as methoxymethyl, ethoxymethyl, n-propoxymethyl, iso-propoxymethyl, n-butoxymethyl, iso-butoxymethyl, sec.-butoxymethyl, tert.-butoxymethyl, n-pentoxymethyl, iso-pent-oxymethyl, sec.-pentoxymethyl, tert.-pentoxymethyl, neo-pentoxymethyl, 1,2-dimethylpropoxymethyl, n-hexoxymethyl, iso-hexoxymethyl, sec.-hexoxymethyl, n-heptoxymethyl, iso-heptoxymethyl, methoxy-1-ethyl, ethoxy-1-ethyl, n-propoxy-1-ethyl, iso-propoxy-1-ethyl, n-butoxy-1-ethyl, iso-butoxy-1-ethyl, sec.-butoxy-1-ethyl, tert.-butoxy-1-ethyl, n-pentoxy-1-ethyl, iso-pentoxy-1-ethyl, sec.-pentoxy-1-ethyl, tert.-pentoxy-1-ethyl, neopentoxy-1-ethyl, 1,2-dimethylpropoxy-1-ethyl, n-hexoxy-1-ethyl, iso-hexoxy-1-ethyl, sec.-hexoxy-1-ethyl, methoxy-2-ethyl, ethoxy-2-ethyl, n-propoxy-2-ethyl, iso-propoxy-2-ethyl, n-butoxy-2-ethyl, iso-butoxy-2-ethyl, sec.-butoxy-2-ethyl, tert.-butoxy-2-ethyl, n-pentoxy-2-ethyl, iso-pentoxy-2-ethyl, sec.-pentoxy-2-ethyl, tert.-pentoxy-2-ethyl, neo-pentoxy-2- ethyl, 1,2-dimethyl-propoxy-2-ethyl, n-hexoxy-2-ethyl, iso-hexoxy-2-ethyl and sec.-hexoxy-2-ethyl, $C_3$–$C_{12}$-cycloalkyl, preferably $C_3$–$C_8$-cycloalkyl, such as cyclopropyl, cyclobutyl, cyclopentyl, cyclohexyl, cycloheptyl and cyclooctyl, halogen, such as fluorine, chlorine, bromine and iodine, preferably chlorine and bromine, arly phenyl, 1-naphthyl, 2-naphthyl, 1-anthryl, 2-antrhyl and 9-anthryl particularly preferably phenyl, $C_7$–$C_{20}$-alkylaryl, preferably $C_7$–$C_{10}$-alkylphenyl, such as 2-methylphenyl, 3-methylphenyl, 4-methylphenyl, 2-ethyl-phenyl, 3-ethylphenyl, 4-ethylphenyl, 2-n-propylphenyl, 3-n-propylphenyl, 4-n-propylphenyl, 2-iso-propylphenyl, 3-iso-propylphenyl, 4-iso-propylphenyl, 2-n-butylphenyl, 3-n-butylphenyl, 4-n-butylphenyl, 2-iso-butylphenyl, 3-iso-butylphenyl, 4-iso-butylphenyl, 2-sec.-butylphenyl, 3-sec.-butylphenyl, 4-sec.-butylphenyl, 2-tert.-butylphenyl, 3-tert.-butylphenyl and 4-tert.-butylphenyl, $C_7$–$C_{20}$-alkoxyaryl, preferably $C_7$–$C_{10}$-alkoxyphenyl, such as 2-methoxyphenyl, 3-methoxyphenyl, 4-methoxyphenyl, 2-ethoxyphenyl, 3-ethoxyphenyl, 4-ethoxyphenyl, 2-n-propoxyphenyl, 3-n-propoxyphenyl, 4-n-propoxyphenyl, 2-iso-propoxyphenyl, 3-iso-propoxyphenyl, 4-iso-propoxyphenyl, 2-n-butoxyphenyl, 3-n-butoxyphenyl, 4-n-butoxyphenyl, 2-iso-butoxyphenyl, 3-iso-butoxyphenyl, 4-iso-butoxyphenyl, 2-sec.-butoxyphenyl, 3-sec.-butoxyphenyl, 4-sec.-butoxyphenyl, 2-tert.-butoxyphenyl, 3-tert.-butoxyphenyl and 4-tert.-butoxyphenyl, aryl which is disubstituted to trisubstituted by $C_1$–$C_8$-alkyl, preferably phenyl which is disubstituted or trisubstituted by $C_1$–$C_4$-alkyl, such as 2,4-dimethylphenyl, 3,4-dimethylphenyl and 3,4,5-trimethylphenyl, aryl which is disubstituted or trisubstituted by $C_1$–$C_8$-alkoxy, preferably phenyl which is disubstituted or trisubstituted by $C_1$–$C_4$-alkoxy, such as 3,4-dimethoxyphenyl and 3,4,5-trimethoxyphenyl, aryl which is monosubstituted, disubstituted or trisubstituted by $C_1$–$C_4$-haloalkyl, preferably phenyl which is monosubstituted, disubstituted or trisubstituted by $C_1$–$C_2$-fluoro- or -chloro-alkyl, particularly preferably phenyl which is monosubstituted, disubstituted or trisubstituted by trifluoromethyl or trichloroethyl, such as 4-trifluoromethylphenyl and 4-trichloromethylphenyl, aryl which is monosubstituted, disubstituted or trisubstituted by $C_1$–$C_4$-haloalkoxy, preferably phenyl which is monosubstituted, disubstituted or trisubstituted by $C_1$–$C_2$-fluoro- or -chloroalkoxy, particularly preferably phenyl which is monosubstituted, disubstituted or trisubstituted by trifluoromethoxy or trichloromethoxy, such as trifluoromethoxyphenyl, aryl which is monosubstituted, disubstituted or trisubstituted by halogen, preferably phenyl which is monosubstituted, disubstituted or trisubstituted by fluorine or chlorine, such as 4-chlorophenyl, 3,4-dichlorophenyl, 4-bromophenyl, 4-fluorophenyl and 4-fluoro-3-chlorophenyl, $C_7$–$C_{20}$-arylalkyl, preferably $C_7$–$C_{10}$-phenylalkyl, such as benzyl, phenethyl, 1-phenyl-n-propyl, 2-phenyl-n-propyl, 3-phenyl-n-propyl, 1-phenyl-iso-propyl, 2-phenyl-iso-propyl, 1-phenyl-n-butyl, 2-phenyl-n-butyl, 3-phenyl-n-butyl, 4-phenyl-n-butyl, 1-phenyl-iso-butyl, 2-phenyl-iso-butyl, 3-phenyl-iso-butyl, 1-phenyl-sec.-butyl, 1-benzyl-n-propyl, 2-phenyl-sec.-butyl, 3-phenyl-sec.-butyl and 1,1-dimethylphenethyl, $C_7$–$C_{20}$-arylalkyl which is monosubstituted, disubstituted or trisubstituted by halogen in the aryl moiety, preferably $C_7$–$C_{10}$-phenylalkyl which is monosubstituted, disubstituted or trisubstituted by fluorine or chlorine in the phenyl moiety, such as 4-fluorobenzyl, 4-chlorobenzyl, 2,4-dichlorobenzyl and 3,4-dichlorobenzyl, $C_7$–$C_{20}$-arylalkyl which is monosubstituted, disubstituted or trisubstituted by $C_1$–$C_8$-alkyl in the aryl moiety, preferably $C_7$–$C_{10}$-phenylalkyl which substituted, disubstituted or trisubstituted by $C_1$–$C_4$-alkyl in the phenyl moiety, particularly preferably $C_7$–$C_{10}$-phenylalkyl which is monosubstituted, disubstituted or trisubstituted by $C_1$–$C_2$-alkyl in the phenyl moiety, such as 4-methylphenyl, 4-ethylbenzyl and 4-methylphenethyl, $C_7$–$C_{20}$-arylalkyl which is monosubstituted, disubstituted or trisubstituted by $C_1$–$C_8$-alkoxy in the aryl moiety, preferably $C_7$–$C_{10}$-phenylalkyl which is monosubstituted, disubstituted or trisubstituted by $C_1$–$C_4$-alkoxy in the phenyl moiety, particularly preferably $C_7$–$C_{10}$-phenylalkyl which is monosubstituted, disubstituted or trisubstituted by $C_1$–$C_2$-alkoxy in the phenyl moiety, such as 4-methoxybenzyl, 4-ethoxybenzyl and 4-methoxyphenethyl, $C_7$–$C_{20}$-arylalkyl which is monosubstituted, disubstituted or trisubstituted by $C_1$–$C_4$-haloalkyl in the aryl moiety, preferably $C_7$–$C_{10}$-phenylalkyl which is monosubstituted, disubstituted or trisubstituted by $C_1$–$C_2$-fluoro- or -chloroalkyl in the phenyl moiety, particularly preferably $C_7$–$C_{10}$-phenylalkyl which is monosubstituted, disubstituted or trisubstituted by trifluoromethyl or trichloromethyl in the phenyl moiety, such as 4-trifluoromethylbenzyl and 4-trichloromethylbenzyl, $C_7$–$C_{20}$-arylalkyl which is monosubstituted, disubstituted or trisubstituted by $C_1$–$C_4$haloalkoxy in the aryl moiety, preferably $C_7$–$C_{10}$-phenylalkyl which is monosubstituted-, disubstituted or trisubstituted by $C_1$–$C_2$-haloalkyl in the phenyl moiety, particularly preferably $C_7$–$C_{10}$-phenylalkyl which is monosubstituted, disubstituted or trisubstituted by trifluoromethyl or trichloromethyl in the phenyl moiety, such as 4-trifluoromethoxybenzyl and 4-trichloromethoxybenzyl, phenyl which is substituted by one, two or three phenoxy groups, phenyl which is disubstituted or trisubstituted by halogen and $C_1$–$C_4$-alkyl, such as 2-methyl-4-chlorophenyl and 3-methyl-4-fluorophenyl, phenyl which is disubstituted or trisubstituted by halogen and $C_1$–$C_4$-alkoxy, such as 3-chloro-4-methoxyphenyl, phenyl which is disubstituted or trisubstituted by halogen and $C_1$–$C_4$-haloalkyl, such as 2-chloro-4-trifluoromethylphenyl phenyl which is disubstituted or trisubstituted by halogen and phenoxy, such as 3-chloro-4-phenoxyphenyl, phenyl which is disubstituted or trisubstituted by $C_1$–$C_4$-alkyl and $C_1$–$C_4$-alkoxy, such as 2-methyl-4-methoxyphenyl, phenyl which is disubstituted or trisubstituted by $C_1$-$C_4$-alkyl and $C_1$-$C_4$-haloalkyl, such as 3-methyl-4-trichloromethylphenyl, phenyl which is disubstituted or trisubstituted by $C_1$-$C_4$-alkyl and phenoxy, such as 2-methyl-4-phenoxyphenyl, phenyl which is disubstituted or trisubstituted by $C_1$-$C_4$-alkoxy and $C_1$-$C_4$-haloalkyl, such as 3-trifluoromethyl-4-methoxyphenyl, phenyl which is disubstituted or trisubstituted by $C_1$-$C_4$-alkoxy and phenoxy, such as 3-methoxy-4-phenoxyphenyl, phenyl which is disubstituted or trisubstituted by $C_1$-$C_4$-haloalkyl and phenoxy, such as 3-trifluoromethyl-4-phenoxyphenyl, phenyl which is trisubstituted by halogen, $C_1$-$C_4$-alkyl and $C_1$-$C_4$-alkoxy, phenyl which is trisubstituted by halogen, $C_1$-$C_4$-alkyl and $C_1$-$C_4$-haloalkyl, phenyl which is trisubstituted by halogen, $C_1$-$C_4$-alkyl and phenoxy, phenyl which is trisubstituted by halogen, $C_1$-$C_4$-alkoxy and $C_1$-$C_4$-haloalkyl, phenyl which is trisubstituted by halogen, $C_1$-$C_4$-alkoxy and phenoxy, phenyl which is trisubstituted by halogen, $C_1$-$C_4$-haloalkyl and phenoxy, phenyl which is trisubstituted by $C_1$-$C_4$-alkyl, alkyl, $C_1$-$C_4$-alkoxy and $C_1$-$C_4$-haloalkyl, phenyl which is trisubstituted by $C_1$-$C_4$-alkyl, $C_1$-$C_4$-alkoxy and phenoxy, phenyl which is trisubstituted by $C_1$-$C_4$-alkyl, $C_1$-$C_4$-haloalkyl and phenoxy, phenyl which is trisubstituted by $C_1$-$C_4$-alkoxy, $C_1$-$C_4$-haloalkyl and phenoxy, $R^1$ and $R^2$ together $(CH_2)_n$, such as $CH_2$, $(CH_2)_2$, $(CH_2)_3$, $(CH_2)_4$, $(CH_2)_5$ and $(CH_2)_6$, preferably $(CH_2)_3$, $(CH_2)_4$, $(CH_2)_5$, $(CH_2)_6$, particularly preferably $(CH_2)_3$ and $(CH_2)_4$, $(CH=CH)_m$, such as $(CH=CH)$, $(CH=CH)_2$, $(CH=CH)_3$, preferably $(CH=CH)_2$, $(CH=CH)_3$ particularly preferably $(CH=CH)_2$, n - from 1 to 6, preferably from 3 to 6, particularly preferably 3 and 4, m - from 1 to 3, preferably 2 and 3, particularly preferably 2.

Of the substances themselves, those compounds are excluded from the listed meanings for the process where $R^1$ and $R^2$ are each halogen and where $R^1$ and $R^2$ are together $(CH=CH)_m$.

The imidazole-2-carboxylic acids obtained are intermediates, for example for preparing drugs or dyes (DE-A-3,428,493).

PREPARATION EXAMPLES

EXAMPLE 1

4,5-Dichloroimidazole-2-carboxylic acid (Compound No. 1)

A mixture of 137 g (1 mol) of 4,5-dichloroimidazole, 414 g (3 mol) of $K_2CO_3$ and 1,000 ml of carbon dioxide was stirred in an autoclave at 200° C. under autogenous pressure for 10 hours. The solid output was pulverized, suspended in 2 l of water and brought to pH 3–4 with concentrated hydrochloric acid while being cooled with ice. The resulting precipitate was filtered off and recrystallized from water to give 136 g (75%) of 4,5-dichloroimidazole-2-carboxylic acid (Compound No. 1); mp. 240° C. (dec.).

The method of Example 1 was also used to prepare the following compounds:

TABLE 1

| Compound No. | Starting material | No. of moles of starting material | No. of moles of $K_2CO_3$ | Reaction temperature | Product | mp. | Yield |
|---|---|---|---|---|---|---|---|
| 2 | (imidazole with CH$_3$, CH$_3$ substituents) | 1 | 3 | 180° C. | (2-carboxylic acid, CH$_3$, CH$_3$) | 190° C. dec. | 68% |
| 3 | (imidazole with CH$_3$, Cl substituents) | 1 | 2 | 200° C. | (2-carboxylic acid, CH$_3$, Cl) | 270° C. dec. | 66% |

EXAMPLE 2

Benzimidazole-2-carboxylic acid (Compound No. 4)

A mixture of 118 g (1 mol) of benzimidazole, g (2 mol) of K2CO3 and 400 ml of liquid carbon dioxide was stirred in an autoclave at 250° C. under autogenous pressure for 10 hours. The solid output was pulverized, suspended in 2.5 L of water and brought to pH 3–4 with concentrated hydrochloric acid while being cooled with ice. The resulting precipitate was filtered off and recrystallized from water to give 118 g (73%) of benzimidazole-2-carboxylic acid (Compound No. 4); mp. 170° C. (dec.).

The method of Example 2 was used to prepare the following compounds:

TABLE 2

| Compound No. | Starting material | No. of moles of starting material | No. of moles of K₂CO₃ | Reaction temperature | Product | mp. | Yield |
|---|---|---|---|---|---|---|---|
| 5 | Cl-benzimidazole | 1 | 2 | 250° C. | Cl-benzimidazole-COOH | 155° C. dec. | 55% |
| 6 | H₃C-benzimidazole | 1 | 2 | 250° C. | H₃C-benzimidazole-COOH | 140° C. dec. | 50% |

We claim:

1. A process for preparing a 4,5-disubstituted imidazole-2-carboxylic acid, which comprises reacting a 4,5-disubstituted imidazole with carbon dioxide under superatmospheric pressure at from 150° to 300° C. in the presence of a base.

2. The process for preparing a 4,5-disubstituted imidazole-2-carboxylic acid of the formula I

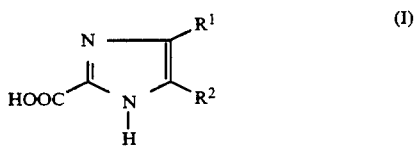

where the substituents $R^1$ and $R^2$ are each independently of $C_1$–$C_{20}$-alkyl, $C_2$–$C_{20}$-alkoxyalkyl, $C_3$–$C_{12}$-cycloalkyl, halogen or unsubstituted or $C_1$–$C_8$-alkyl-, $C_1$–$C_8$-alkoxy-, halogen-, $C_1$–$C_4$-haloalkyl-, $C_1$–$C_4$-haloalkoxy- or phenoxy-substituted aryl or $C_7$–$C_{20}$-arylalkyl or are together unsubstituted or $C_1$–$C_8$-alkyl-, $C_1$–$C_8$-alkoxy- and/or halogen-monosubstituted or -disubstituted $(CH_2)_n$ or $(CH=CH)_m$, where n is from 1 to 6 and m is from 1 to 3, by reacting a 4,5-disubstituted imidazole with carbon dioxide as in claim 1.

3. The process for preparing a 4,5-disubstituted imidazole-2-carboxylic acid of claim 1, wherein the reaction is carried out in the presence of an inorganic carbonate, bicarbonate and/or hydroxide.

4. The process for preparing a 4,5-disubstituted imidazole-2-carboxylic acid of in claim 1, wherein the reaction is carried out in the presence of an alkali metal bicarbonate, alkali metal or alkaline earth metal carbonate and/or alkali metal or alkaline earth metal hydroxide.

5. The process for preparing an imidazole-2-carboxylic acid I of claim 1, wherein the reaction is carried out under a pressure of from 10 to 300 bar in the presence of an alkali metal carbonate, bicarbonate and/or hydroxide.

6. The process for preparing an imidazole-2-carboxylic acid I of claim 1, wherein the reaction is carried out under a pressure of from 40 to 180 bar at from 180° to 280° C. in the presence of from 1 to 5 mol % of an alkali metal carbonate, bicarbonate and/or hydroxide.

7. The process for preparing an imidazole-2-carboxylic acid I of claim 1, wherein the reaction is carried out under a pressure of from 40 to 180 bar at from 180° to 280° C. in the presence of from 1 to 3.5 mol % of potassium carbonate.

* * * * *